(12) United States Patent
Yamashiro

(10) Patent No.: US 6,520,903 B1
(45) Date of Patent: Feb. 18, 2003

(54) MULTIPLE MODE PHOTONIC STIMULATION DEVICE

(76) Inventor: Patsy Yukie Yamashiro, 9918 N.E. 116 th St., Kirkland, WA (US) 82806

( * ) Notice: Subject to any disclaimer, the term of this patent is extended or adjusted under 35 U.S.C. 154(b) by 0 days.

(21) Appl. No.: 09/572,959

(22) Filed: May 18, 2000

(51) Int. Cl.[7] ................ A61B 17/52; A61N 2/00
(52) U.S. Cl. ........................................... 600/9
(58) Field of Search ................. 600/9, 10, 11, 600/12, 13, 14, 15, 27, 28, 26; 601/25; 607/1, 69, 88

(56) References Cited

U.S. PATENT DOCUMENTS

| | | | | |
|---|---|---|---|---|
| 3,773,049 A | * | 11/1973 | Rabichev et al. | 600/28 |
| 5,067,940 A | * | 11/1991 | Liboff et al. | 600/13 |
| 5,108,361 A | * | 4/1992 | Hein | 600/28 |
| 5,474,528 A | * | 12/1995 | Meserol | 601/15 |
| 5,908,444 A | * | 6/1999 | Azure | 600/14 |
| 5,947,908 A | * | 9/1999 | Morris | 600/27 |
| 6,234,953 B1 | * | 5/2001 | Thomas et al. | 600/14 |

* cited by examiner

Primary Examiner—Max F. Hindenburg
Assistant Examiner—Brian Szmal

(57) ABSTRACT

An electromagnetic stimulation device that generates combined repetitive pulses of full spectrum light and magnetic field to promote propagation of energy and pain relief in the body. The level of currents induced by the pulsed magnetic field stimulation alone is limited in magnitude to values below the expected normal threshold of motor nerve stimulation. Broad spectrum pulses of light and magnetic field are used to satisfy multiple resonance and wavelength criteria for enhancing energy transfer. The measurement of the magnitude of induced magnetic field at different body sites is used for the assessment of effectiveness of stimulation.

9 Claims, 2 Drawing Sheets

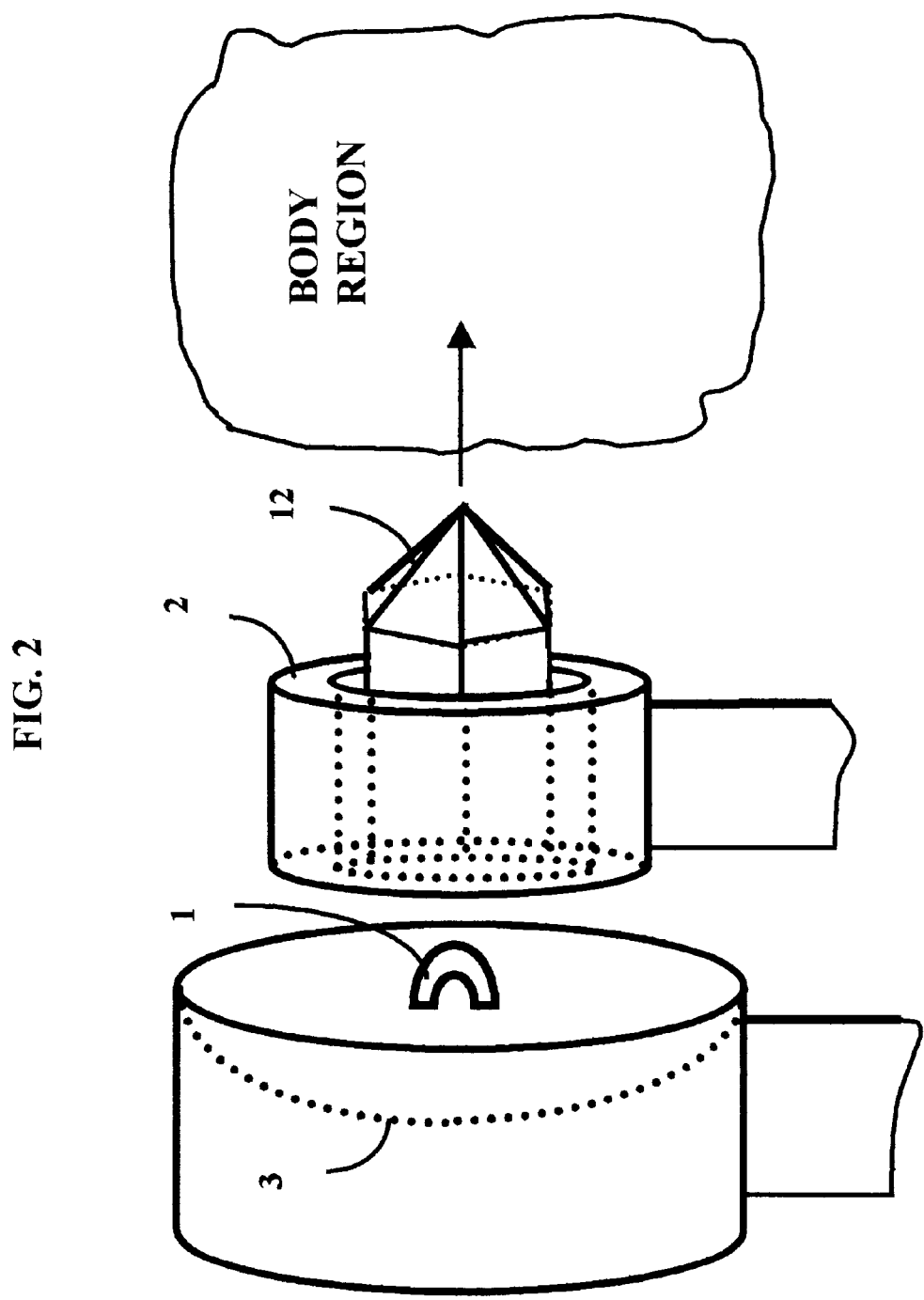

MULTIPLE MODE PHOTONIC STIMULATION DEVICE

BACKGROUND

1. Field of Invention

This invention relates to the use of synchronized pulsed magnetic field and light photon stimulation to excite human or animal tissue including nerves or acupuncture points for pain control or energetic enhancement purposes.

2. Description of Prior Art

Heretofore, electromagnetic stimulation of sensory nerves or acupuncture points has focused mainly on stimulation of nerve tracts for the purpose of promoting release of natural opiates or pain pathway blocks through gating mechanisms. Various forms of such stimulation have been tried such as application of voltages or currents to acupuncture needles, transcutaneous electrical nerve stimulation (TENS), pulsed magnetic field stimulation, local application of heat or cold, use of light radiation, and magnetic therapy. Prior art devices of this type include the use of low frequency magnetic pules as described in U.S. Pat. No. 6,234,953 B1, issued May 22, 2001. Application of voltages or currents to needles and TENS both involve passage of electrical current through superficial skin and tissue which is known to be prone to stimulation of pain fibers. The magnitude of stimulation is then limited to what a given subject can tolerate. Pulsed magnetic field stimulation relies on induced currents, which can largely avoid pain fiber stimulation and so is capable of higher levels of nerve stimulation. However, pulsed magnetic field stimulation at intensities high enough for neural stimulation requires cumbersome apparatus with a many limitations. These limitations arise from the high energy requirements and associated limitations of coil heat generation, time required for recharging of energy storage devices as capacitors, and physical apparatus size. Traditional acupuncture is postulated to also involve meridian pathways, which is not limited to known nerve tracts. These pathways are felt to involve body energy management and overall maintenance of health. While many different attempts have been made to stimulate or increase the energy level within these meridians, no scientifically acceptable means of assessing or measuring the energy states of body areas, acupuncture points, or meridians currently exists. The electrical potential, resistance, or impedance has been measured between acupuncture points or a given acupuncture point and surrounding tissue, but the known unreliability and lack of specificity of such measurements limited their use in energy state assessment. Some of these complications include: variable impedance of the overlying skin layer, contact potentials which change with minor perturbations, and complex nature of tissue impedance with frequency dependent properties. Thus, the effectiveness of any method in stimulating a given acupuncture point or changing the energy status of the meridian system and the body remains open to question and highly variable in result. The specific form of what constitutes the most effective way to stimulate specific acupuncture points or the meridian system electromagnetically then remains unclear. Pulsed magnetic field stimulation has been previously found to be able to stimulate nerves and even muscles in essentially a painless way. However, apparatus and procedures necessary to insure that the stimulus energy reaches the meridians or other parts of the body have not been previously described. Magnetic therapy involving applying permanent magnets to the body surface has been previously tried with positive therapeutic results, but this procedure is limited in application due to the necessity of constantly wearing magnets. Techniques for directly magnetizing the human or animal body as a form of magnetic therapy have not been previously described.

Prior work have also shown that other modes of sensory stimulation made in the vicinity of sources of pain can also be used to alleviate pain or also stimulate acupuncture points. Some of these modes include application of cold massage, light, pressure, and heat. In general, pain relief can be provided by a wide variety of sensory stimulation. Prior art applications of sensory stimulation include: application of monochromatic light and biofeedback as specified in U.S. Pat. No. 5,947,908 issued on Sep. 7, 1999, application of heat, light, sound, and VHF electromagnetic radiation for central nervous system stimulation as specified in U.S. Pat. No. 3,773,049 issued on Nov. 20, 1973, and application of acoustic, optical, mechanical, and/or electrical signals with increasing or decreasing frequency as specified in U.S. Pat. No. 5,108,361 issued on Apr. 28, 1992. Thus, a reasonable strategy to maximize pain relief is to combine as many modalities as possible. Some use has been made of combined modes such as pressure and electricity in electrical stimulation of needles or TENS and magnetic stimulation, but such combinations have not been previously fully exploited. Specifically, the combined use of pulsed magnetic field in synchrony with full spectrum pulsed light has not been tried for acupuncture point or body energy stimulation. From a quantum mechanical viewpoint, light and magnetic field can be considered as both photons, that can supply energy. Body tissue components have a magnetic moment that is capable of resonance and magnetization effects. Nuclear magnetic resonance and imaging is an example where this type of resonance is applied for a medical application. Prior art attempts at exploiting resonance include application of a fluctuating magnetic field to excite postulated ionic cyclotron resonance as specified in U.S. Pat. No. 5,067,940 issued on Nov. 26, 1991 and use of a complex frequency pulsed electromagnetic generator as specified in U.S. Pat. No. 5,908,444 issued on Jun. 1, 1999. Whether ion cyclotron resonance actually occurs in tissue has not been conclusively demonstrated to date, also the specific form of stimulation used in this approach does not fully exploit particle properties. The specific combination of light and magnetic field required for effectively exploiting these resonance or other effects for enhanced energetic stimulation of the human or animal body has not been previously described.

OBJECTS AND ADVANTAGES

Accordingly, to provide an effective way to photonically stimulate tissue and modify the energy level in the body, a stimulation device is needed which has specific characteristics which match the energy transporting mechanisms of the body. Magnetic stimulation has important advantages over electrical stimulation in being able to avoid stimulation of pain fibers and not required needle insertion or electrode application. The present invention was designed to incorporate magnetic in combination with light stimulation to permit energetic excitation in a manner that could be used by a patient for self-use or applied by a practitioner. Light and magnetic field is known to interact in a transient plasma state to produce unique energy waves that propagate in the longitudinal rather than in the customary transverse electric and magnetic field mode. The longitudinal mode of propagation is known by those skilled in the art to be associated with mechanical vibrations and to involve less propagation loss than the transverse electric and magnetic field mode.

The preferred embodiment of the present inventive device incorporates a xenon flash tube that generates a transient plasma state. Energetic excitation involving internally induced currents is another of the advantages of the inventive method in that the externally induced currents present in many previous acupuncture stimulators is not required. Another object of the present invention is to permit magnetization of major body areas as a way to provide magnetic therapy without encumbering the subject with the necessity of constantly wearing permanent magnet. Another object of the present invention is to provide a way to verify the effectiveness of the stimulator in providing energy to the body and level of magnetization. Such a measurement also forms the basis for a diagnostic assessment of the health of the body area and a rationale for treatment by use of the stimulator to promote a normal status. Another object of the present invention is to incorporate auditory sensory stimulation simultaneously with magnetic and light stimulation as a way of increasing total sensory stimulation to enhance pain relief.

SUMMARY OF THE INVENTION

The present invention provides for the above stated objectives as well as others by providing an electromagnetic stimulation device, which generates combined repetitive pulses of light and magnetic field to promote propagation of energy in the body. The level of currents induced by the pulsed magnetic field stimulation alone is limited in magnitude to values below the expected normal threshold of nerve fiber stimulation. When previously described apparatus used for pulsed magnetic field stimulation is used under this constraint, in effective pain control results. Also, there have been no previously reports on energy propagation under these conditions. It will be apparent to those skilled in the art that conventional electromagnetic theory cannot justify the current rationale, but consideration of quantum electrodynamics effects is necessary. According to quantum theory, at least two major energy levels and associated frequencies are present in hydrated tissue and any magnetically sensitive material. Probabilities are connected with these levels that can be affected by the light and magnetic field levels. Nuclear magnetic and ionic resonances are possible in tissue by judicious choices of these levels and the frequencies involved. In general, a variety of magnetic resonant frequencies and wavelengths of light are necessary to promote effective energy transfer. The approach here is to satisfy these requirements by using broad-spectrum pulses of magnetic field and light to insure a stimulus with sufficient harmonic content to promote effective energy transfer. In addition, full spectrum light provided by a flash tube such as zenon is used to insure that the proper wavelength is present for such transfer to occur. A unique property of flash tube discharges is the transient creation of a plasma state. Plasma is created by the interaction of electrons and positive gas ions during a discharge. A plasma resonant frequency is generated during the discharge along with a longitudinally propagated wave. This wave is characterized by special properties known to those skilled in the art that allow the focusing of energy and control of plasma resonant frequency by using an externally applied magnetic field. Cyclotron resonance is known to be possible with plasma waves interacting with a directed magnetic field. The density of the gas within the gas tube determines the plasma resonant frequency. Density can then be chosen for maximum effectiveness of energetic stimulation by matching the resonant frequency of key cellular energetic processes such as those involved in ATP utilization. Thus, magnetic field and electric field can be simultaneously applied longitudinally in the desired direction of propagation. This is in contrast to conventional electromagnetic waves where the electric and magnetic fields are in the transverse mode that is perpendicular to the direction of propagation. In this way, resonance requirements for enhancement of energy stimulation can be met by providing stimuli which have temporal characteristics to meet resonance criteria for enhanced energy transfer, and full light spectrum to meet associated wavelength criteria for enhancement. Magnetic pulses of the stimulator provided for herein are generated by a capacitive discharge circuit where ordinary power line alternating current (50–60 Hz) or a battery powered oscillator signal is used to charge capacitors to steady levels. Individual stimulus pulses are formed by discharging these capacitors into a single or multiple coils using a switching device such as a silicon controlled rectifier and xenon flash tube for magnetic field and light generation. By appropriate choice of total circuit capacitance, coil inductance, and resistance a unidirectional magnetic field is generated. Pulses will be repeated according to a repetition rate that is set to obtain optimum magnetic field transfer. The coil system with or without the flash tube is mounted on a handle and connected with flexible wires to the main electronics unit to allow positioning of the coil and resultant magnetic field at various locations.

The present device allows for the creation of the proper conditions for multiple body tissue resonance to occur and exploits this condition to promote transmission of magnetic field into the meridian or other body system. Use of monopolar magnetic stimulation pulses and light pulses permit magnetization of target body areas which creates residual magnetic effects suitable for magnetic therapy even after the stimuli crease. The measurement of the magnitude of magnetic field at different areas of the body then provides a way to assess the effectiveness of stimulation as well as a basis of evaluating the state of the body energy system. Such measurements can be made during as well as before and following stimulation.

Preliminary studies performed indicate that the combined and simultaneous treatment of the inventive device provides a substantially greater degree of pain relief and energetic enhancement (degree of magnetization) than either magnetic or light stimulation alone.

BRIEF DESCRIPTION OF THE SEVERAL VIEWS OF THE DRAWING

The invention will now be described with reference to the accompanying drawings in which:

FIG. 2 shows an embodiment where natural quartz crystal between the flash tube and body surface being stimulated.

DETAILED DESCRIPTION OF THE INVENTION

Figure 1:
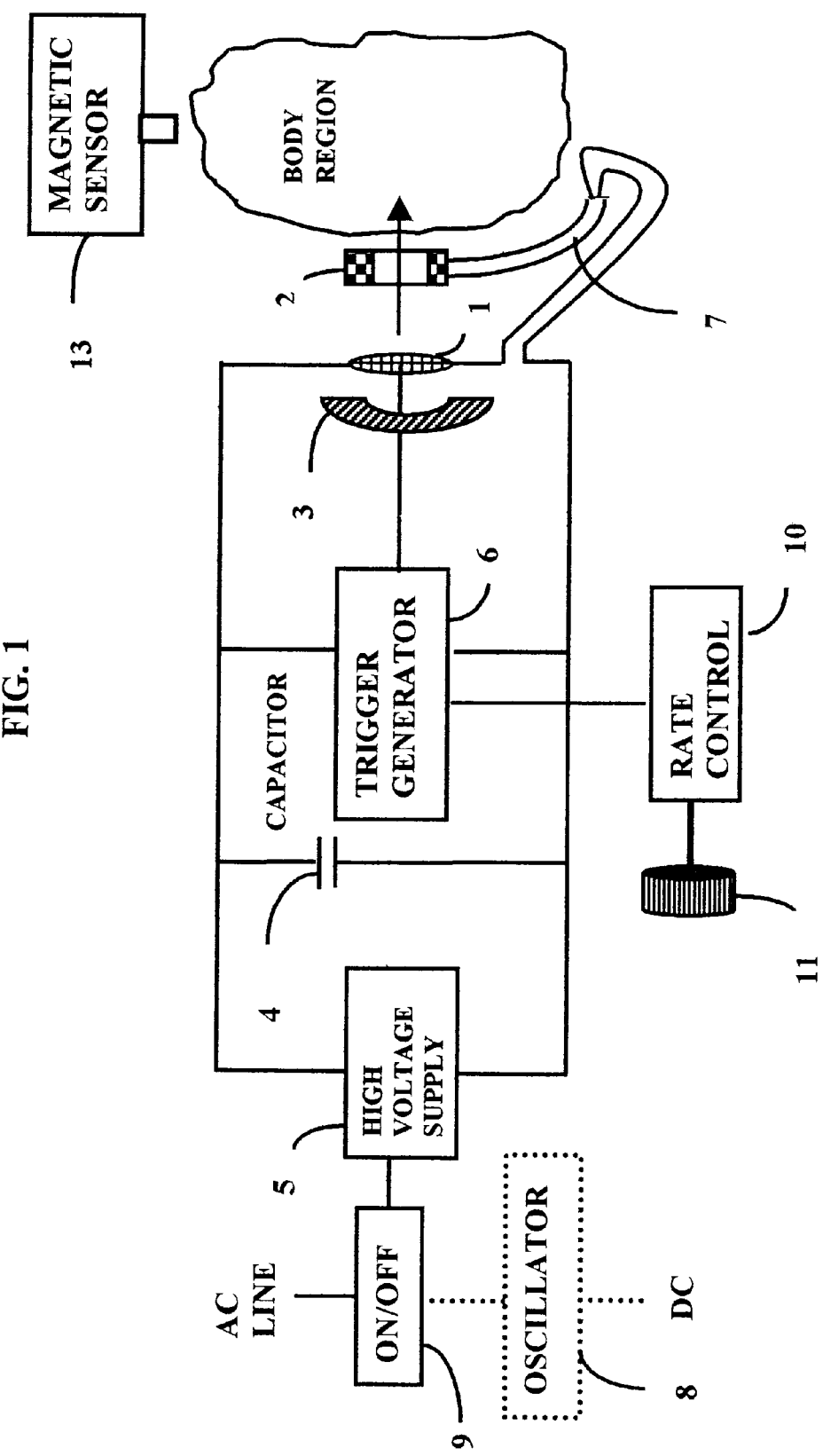
FIG. 1 is a schematic diagram of the apparatus.

Referring to FIG. 1, the schematic block diagram of the inventive stimulating apparatus is illustrated. Magnetic stimulator coil 2 is coupled in an electrical series connection with a full spectrum flash tube 1 so that each share the same excitation current. Electrical circuits required for the flash tube excitation at adjustable rates are well known in the art. Excitation current is derived from discharging a capacitor 4 that is previously charged by high voltage supply 5. On-off switch 9 connects high voltage supply 5 to AC or alternating current power. Alternatively, high voltage supply 9 can be powered by oscillator 8 which converts DC or direct current battery power to alternating current. The major innovations of the present apparatus include the addition of a stimulating coil 2 in series connection with the flash tube 1 and the synchronous use of both light and magnetic field pulses for energetic stimulation of the human body. Effective human energetic stimulation also require a unique specific combination of stimulator design characteristics. From a quantum mechanical viewpoint, both light and magnetic field can be considered as photonic energetic stimuli. Thus, the first advantage of a combined light and magnetic field stimulator is to be able to achieve higher total energy levels while still limiting the stimulus levels of both. This is significant because stimulation levels generally set the limit on device effectiveness. For example, in transcutaneous electrical nerve stimulation (TENS) the use of electrical stimulation usually leads to stimulation of pain fibers in the vicinity of the local site of stimulation. Although TENS effectiveness for relief of an existing pain improves as stimulation level increases, the additional stimulus site pain ultimately limits the level of pain control. In TENS, stimulus level is usually adjusted to the maximum that a given subject is willing to tolerate. In pulsed magnetic field stimulation (PMFS) pain fiber stimulation does not seem to present a problem, but the use of high levels will ultimately lead to stimulation of even motor nerves. Motor nerve stimulation would be undesirable when the objective of the stimulation is pain control. High level PMFS is also limited in the total possible treatment time due to heat buildup by the stimulating coil. Pulse repetition rates for high level PMFS is also limited to below about 1 per second due to recharge requirements. Pulse repetition rates up to 10 per second have been used with success with TENS, so the repetition rate limitation for high level PMFS undoubtedly limits effectiveness of this approach for pain control. The design approach of the present apparatus purposely limits coil stimulation in terms of the rate of current rise to below $10^8$ ampere-turns per second maintained for 100 microseconds. The product of the two preceding numbers, 10,000 ampere-turns, sets the strength-duration threshold for motor neuron excitation. Application of this limit leads to significantly lower current requirements and permits the use of conventional flash tube circuits for coil excitation well known to those skilled in the art. Use of a xenon flash tube is advantageous because of the full spectrum and high output power property of such light. This facilitates meeting wavelength requirements of any resonance process involved in body energetics. The narrow pulse width of flash tube discharges also facilitates meeting resonant frequency requirements since narrow width pulses inherently have a wide frequency bandwidth. Relatively narrow width pulses are also used for magnetic stimulation that also have similar advantages for meeting magnetic resonance frequency requirements. Flash tube designs commonly use inductors in electrical series with the flash tube to improve the sharpness of light flashes. Light flash durations measured in microseconds are typical. The design approach here is to substitute the magnetic stimulation coil in place of such an inductor. In this way, the stimulation coil acts to shape the light pulse as well as provide a magnetic field for body stimulation. Electronic circuitry required to vary the repetition rate of pulses over a range of 1 to 100 pulses per second is well known to those skilled in the art and is represented in FIG. 1 as rate control 10. Provision for rate control extends the capability of matching to body energetic resonant frequencies that have been postulated to occur within 1–100 cycles per second. Rate control 10 can be implemented by using variable resistive-capacitive current charging to conduction thresholds of neon tubes. Different repetition rates are then obtained by setting the resistance value with a potentiometer 11 shown in FIG. 1. Rate control 10 output is connected to trigger generator 6 either directly or through a silicon controlled rectifier switch. Trigger generator 6 creates the high voltages required for flash tube conduction. Other standard timing circuits can be used as well and are well known to those skilled in the art. By choosing appropriate values of circuit parameters, a monopolar stimulus current which generates a positive magnetic field at the coil surface nearer to the body surface being stimulated. For example, a storage capacitance of 7 microfarads charged to 440 volts discharged through a coil inductance of 200 microhenries (corresponding approximately to 70 turns of AWG 12 enameled copper wire of average radius 0.75 inch) and 1 ohm flash tube resistance is expected to be associated with a peak current of 75 amps. The waveform for this case is monopolar with a stimulus rise time (10%–90% transition) less than 50 microseconds and the fall time (90%–10%) greater than 250 microseconds during recovery. The specific durations are not critical, and other durations could be used, however the rise time must be shorter than fall time to insure generation of induced current in the body primarily in one direction. During use, the magnetic stimulation coil 1 is positioned directly over or touching the body surface. The coil consists of multiple turns of wire made either around a non-magnetic coil form or flat-spiral arrangement. Non-magnetic coil forms that satisfy requirements could be made of polyurethane or nylon. Enamel coating or other non-magnetic and non-conducting material insulates coil wire. An air space is provided at the center of the coil that can be positioned for passage of light generated from flash coil 2 to the body surface. A curved handle 7 is attached to the stimulating coil 2 such that the handle curvature starts at the coil and curves towards the body surface as shown in FIG. 1. The purpose of the curvature is to allow identification of the proper coil polarity by feel alone. Flash tube 1 is positioned in conjunction with a reflector 3 to direct light towards the body surface. Reflector 3 is made of polished aluminum or plastic with a reflecting or white surface. Flash tube 1 can be mounted together with stimulating coil 2 or separately as shown in FIG. 2. [Depending on the purpose of stimulation, close proximity of light and magnetic stimulation over a common body surface could be advantageous or separate locations of light and magnetic field could be used.] A reflector positioned around the flash tube is used to concentrate light to specific spatial regions. Light emanating from the flash tube can be further enhanced in terms of conditions at a specific body surface by optical filtering which consist of positioning focusing lens or optically active materials such as quartz crystal between the flash tube and body surface during energy enhancement procedures. FIG. 2 shows such an embodiment where a natural quartz crystal 12 is positioned in the optical path between the flash tube 1 and the body region to be stimulated. The quartz crystal 12 in FIG. 2 is also placed within the magnetic field produced by coil 2. The arrangement of FIG. 2 facilitates the interaction of light and magnetic field within quartz crystal 12 for enhanced stimulation effect on the body surface. The stimulating coil also serves the purpose of focusing longitudinal mode plasma electromagnetic waves for stimulation and provides a means to alter the resonant frequency of the plasma wave. The property of a directed magnetic field to focus plasma waves is well known to those skilled in the art. Quartz will also provide an additional way to focus and tune the plasma wave. Determining the effectiveness of various strategies can only be made based on a quantitative measurement. The index of energetic stimulation level used by the present approach is the degree of magnetization of the body area involved. Magnetic sensor 13 in FIG. 1 is a magnetometer or device for measuring magnetic field at levels comparable to the strength of the earth's magnetic field with a direct meter readout. Various types of sensor units can be used which include SQUIDS (superconducting quantum interference device), electron and proton resonance transducers, pickup coils and Hall effect sensors. The response time of such a sensor must be less than about 10 seconds time constant to permit measurements to be made minute by minute. Measurement of the degree of magnetization also includes tissue responses to plasma wave excitation that can occur at plasma resonance frequencies. Positioning magnetic sensor 13 directly over the body part of interest before and following application of stimulation with the present apparatus allows quantitation of the level of magnetization achieved as well as the persistence of magnetization. Such quantitation of effect is especially useful in dealing with assessing effects on uncooperative subjects or animals where verbal feedback is lacking. The ionic content of body tissues insures the existence of a net magnetic moment and persistence of a magnetic field following stimulation. The presence of a negative magnetic field near the body surface is felt to lead to positive therapeutic effects in terms of cellular repair and pain control. The present stimulation device generator a pulsed magnetic field over the body surface, which leads to an induced negative magnetic field, which persists even following stimulation when used as described above. The degree of magnetization and persistence reflects energy level of the body area, which will be affected by both magnetic and light stimulation.

The coil handle is provided with a curvature to permit identification by feel of coil direction. Provision can be made to change the direction of magnetic field by rotating the coil by 180 degrees or a switch. Auditory signals are also generated in synchrony with pulsed stimuli as an additional mode of sensory stimulation as well as an indication of stimulation. One method of auditory signal generation is to use coils that have a hard insulation such as enamel would loosely enough to permit the wires to make a clicking sound when current is pulsed through the coil. It would also be possible to use a signal derived from the stimulation trigger or output current to generate a sound in synchrony with stimulation using a loudspeaker. Simultaneous light and magnetic field stimulation is accomplished either with the flash tube placed in the vicinity or adjacent to the coil system. When a stimulation subject is not blindfolded, visual stimulation is also possible as an additional mode of sensory stimulation by the flash tube discharge. While the above description contains many specificities, these should not be construed as limitations on the scope of the invention, but as an exemplification of one preferred embodiment thereof. Many other variations are possible. A stimulating coil in the above description is referred to as an individual unit, yet it is clear to those skilled in the art that an inductive effect and magnetic field generation is possible from just the flash tube itself or wires used to interconnect components. Thus a possible embodiment which is fully compatible within the scope of the invention is one where a separate stimulating coil is not used. FIG. 2 shows an embodiment where the stimulating coil and flash tube are separately mounted. For an application where maximum portability is desired, combining the coil and flash tube into one hand held unit would be a preferred mode. Multiple coils or stimulating units could also be used in other embodiments to stimulate more than one body site at the same time. Multiple stimulating units could be used in synchronized or asynchronous manner using techniques familiar to those skilled in the art. Use of a xenon flash tube has been described as advantageous, but other sources of full spectrum pulsed light and/or plasma can be used. Accordingly, the scope of the invention should be determined not by the embodiments illustrated, but by the appended claims and their legal equivalents.

I claim:

1. Energetic human or animal body stimulation device comprising a means for generating monopolar magnetic field pulses; a means for producing simultaneous full spectrum light flashes; a means for producing simultaneous plasma discharge; a means for positioning said plasma discharge in proximity to said monopolar magnetic field such as to allow focusing of stimulation energy; each pulse having a leading edge phase which rises or falls to a maximum or minimum magnetic field level in less time than the trailing edge phase where the pulse returns to the baseline level; and a plurality of pulses being generated by a means of controlling the time interval between sequential pulses and light flashes.

2. The stimulator of claims 1 combined with a means for simultaneous or pre or post stimulation measurement of electromagnetic field including that field associated with said plasma discharge at one or more body sites wherein such measurements are used to optimized the stimulator characteristics or assess the effectiveness of stimulation.

3. The stimulator of claims 1 or 2 combined with a means for simultaneous visual stimulation of the subject.

4. The stimulator of claims 1 or 2 combined with a means for simultaneous generation of sounds for auditory stimulation of the subject.

5. The stimulator of claims 2, 3, or 4 wherein said simultaneous or pre or post stimulation measurements of electromagnetic field at one or more body surface points are used for diagnostic interpretation and treatment of the energy state of the body.

6. The stimulator of claims 1, 2, 3, 4, or 5 wherein the stimulating coil or plurality of stimulating coils is mounted on a handle with a curvature wherein coil orientation is identified by tactile feel only.

7. The stimulator of claim 1 wherein said light flash is directed to pass through a means of filtering prior to application to the subject.

8. The stimulator of claims 1, 2, 3, 4, 5, 6, or 7 wherein the purpose of stimulation is to alleviate pain in a patient.

9. The stimulator of claim 6 wherein said stimulating coil or plurality of stimulating coils are mounted on a handle or plurality of handles wherein each handle has a curvature such that coil orientation is identified by tactile feel only.

* * * * *